United States Patent [19]

Roberge et al.

[11] Patent Number: 5,879,902
[45] Date of Patent: Mar. 9, 1999

[54] DIAGNOSTIC METHODS AND KITS FOR THE EVALUATION OF THE SYMPATHETIC NERVOUS SYSTEM FUNCTION

[75] Inventors: Andrée G. Roberge, Sainte-Foy; Michel Charest, Château-Richer, both of Canada

[73] Assignee: Neuro-Biotech Inc., Sainte-Foy, Canada

[21] Appl. No.: 876,248

[22] Filed: Jun. 16, 1997

[51] Int. Cl.[6] .............................. C12Q 1/34; C12Q 1/32; C12Q 1/00; G01N 33/53

[52] U.S. Cl. .............................. 435/18; 435/975; 435/26; 435/4

[58] Field of Search .............................. 435/18, 975, 26, 435/4

[56] References Cited

U.S. PATENT DOCUMENTS 3,903,285  9/1975  Umezawa et al. .......................... 435/18
4,032,406  6/1977  Weeks ....................................... 435/18

OTHER PUBLICATIONS

Stewart LC et al., *Ann Rev Bioch*, 1988, 57:551–592.
Ikeno T et al., *Mol Cell Biochem*, 1977, 18(23):117–123.
Geffen LB, *Life Sci*, 1974, 14(9):1593–1604.
Roberge AG et al., *Nutr Res*, 1985, 5:57–63.
Frigon RP et al., *J Biol Chem*, 1978, 253(19):6780–6786.
Fortin D et al., *Comp Biochem Physiol*, 1993, 104B(3):567–575.
Menniti F et al., *J Biol Chem*, 1986, 261(36):16901–16908.
Laduron P, *Biochem Pharmacol*, 1975, 24(5):557–562.
Ogihara T et al., *J Lab Clin Med*, 1975, 85(4):566–575.
Weinshilboum RM et al., *Science*, 1973, 181 (4103): 943–945.
Sapru MK et al., *Acta Psychiatr Scand*, 1989, 80:474–478.
Fujita F et al., *J Neurochem*, 1978, 30:1569–1572.
Galvin M et al., *Psychiatry Res*, 1991, 39:1–11.

*Primary Examiner*—Louise N. Leary
*Attorney, Agent, or Firm*—Swabey Ogilvy Renault; France Côté

[57] ABSTRACT

The present invention relates to an in vitro diagnostic method for the determination of specific dopamine-β-hydroxylase activity for the evaluation of the sympathetic nervous system function of a patient from a serum sample; which comprises the steps of: a) filtering the serum sample to substantially remove drugs and endogenous inhibitors of dopamine-β-hydroxylase; b) incubating the filtered sample of step a) with a substrate of dopamine-β-hydroxylase for conversion in a detectable compound; c) determining the amount of detectable compound to evaluate dopamine-β-hydroxylase activity and comparing with a normal sample; whereby an amount lower than a normal sample is indicative of a reduced sympathetic nervous system function and an amount higher than a normal sample is indicative of an increased sympathetic nervous system function. A reduction in the sympathetic nervous system function is indicative of neurodegenerative, neuroendocrine, psycho-affective and cardiovascular diseases, burn-out, and chronic fatigue, and the effects of stress such as panic syndrome. An increased in the sympathetic nervous system function is indicative of the effects of stress.

21 Claims, 10 Drawing Sheets

DBH specific activity
nmol of octopamine formed . mL$^{-1}$. min$^{-1}$

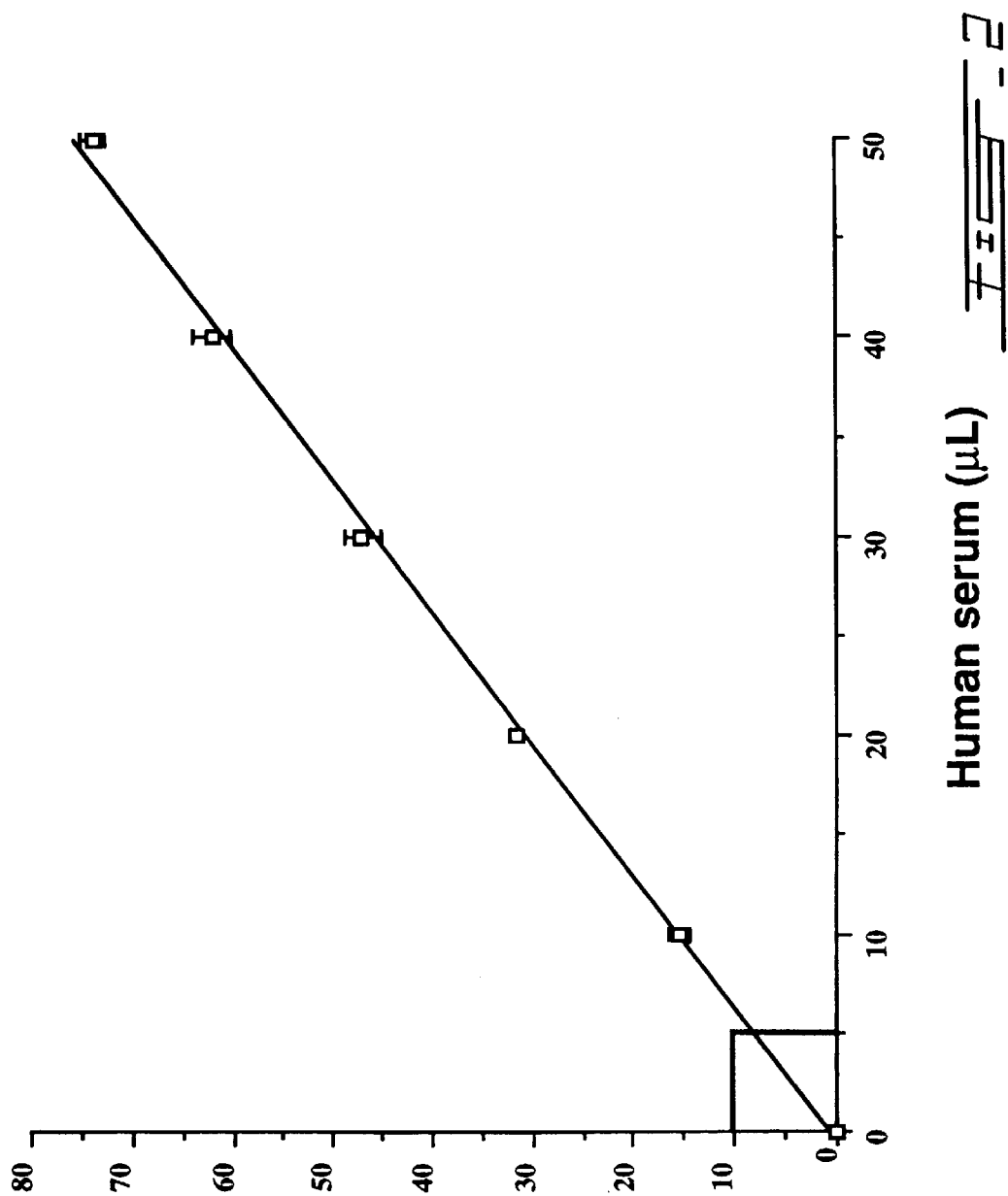

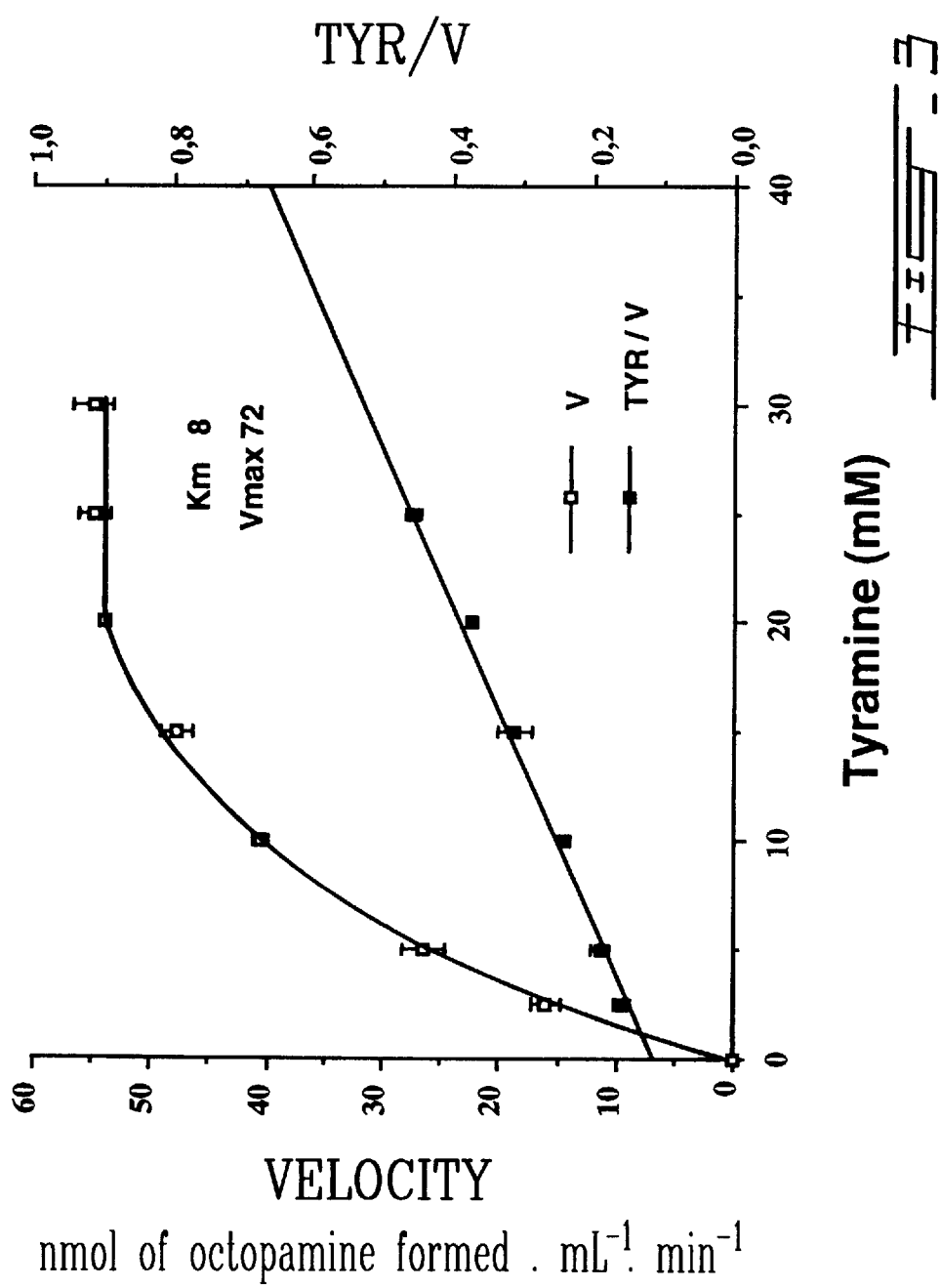

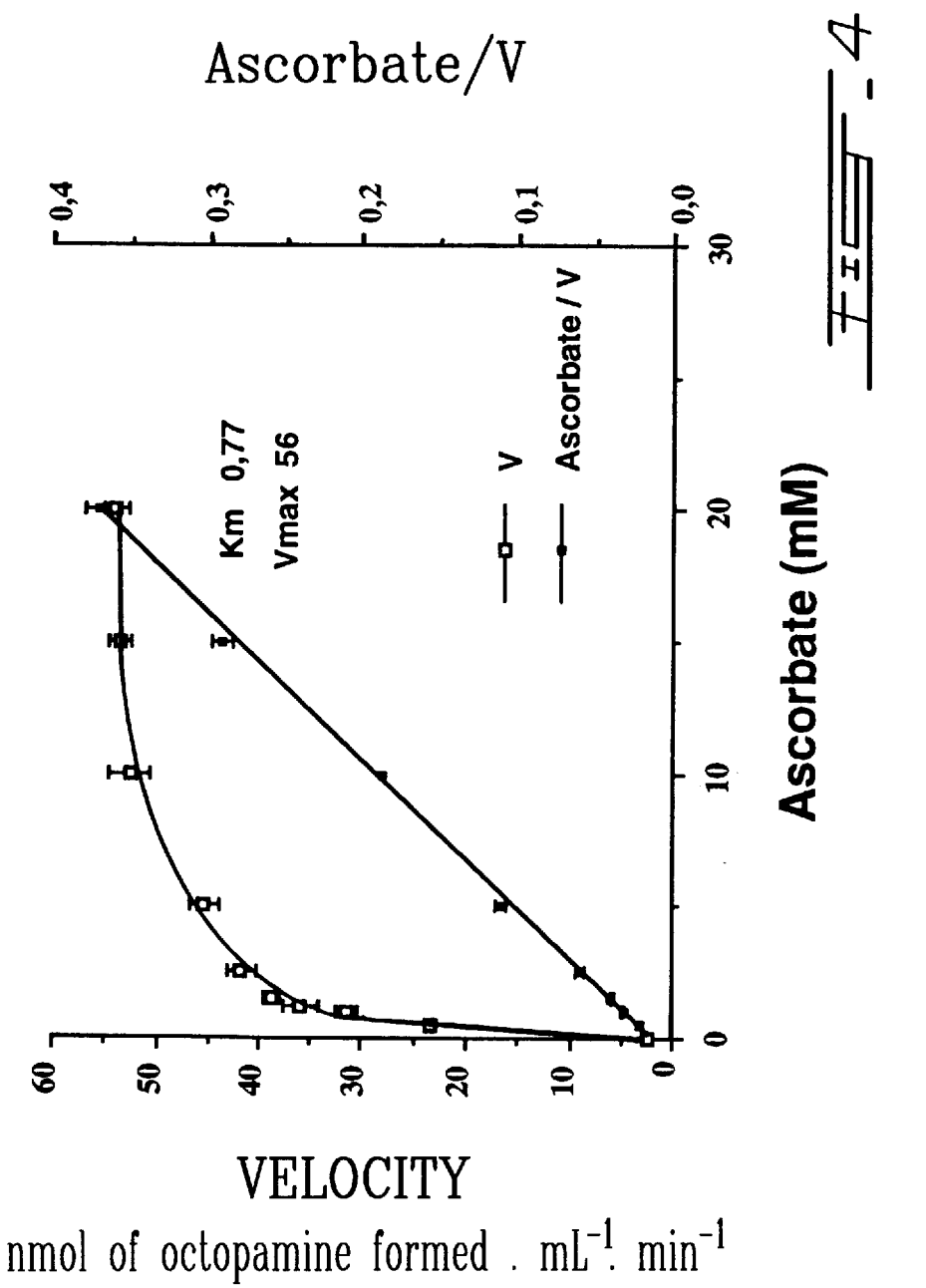

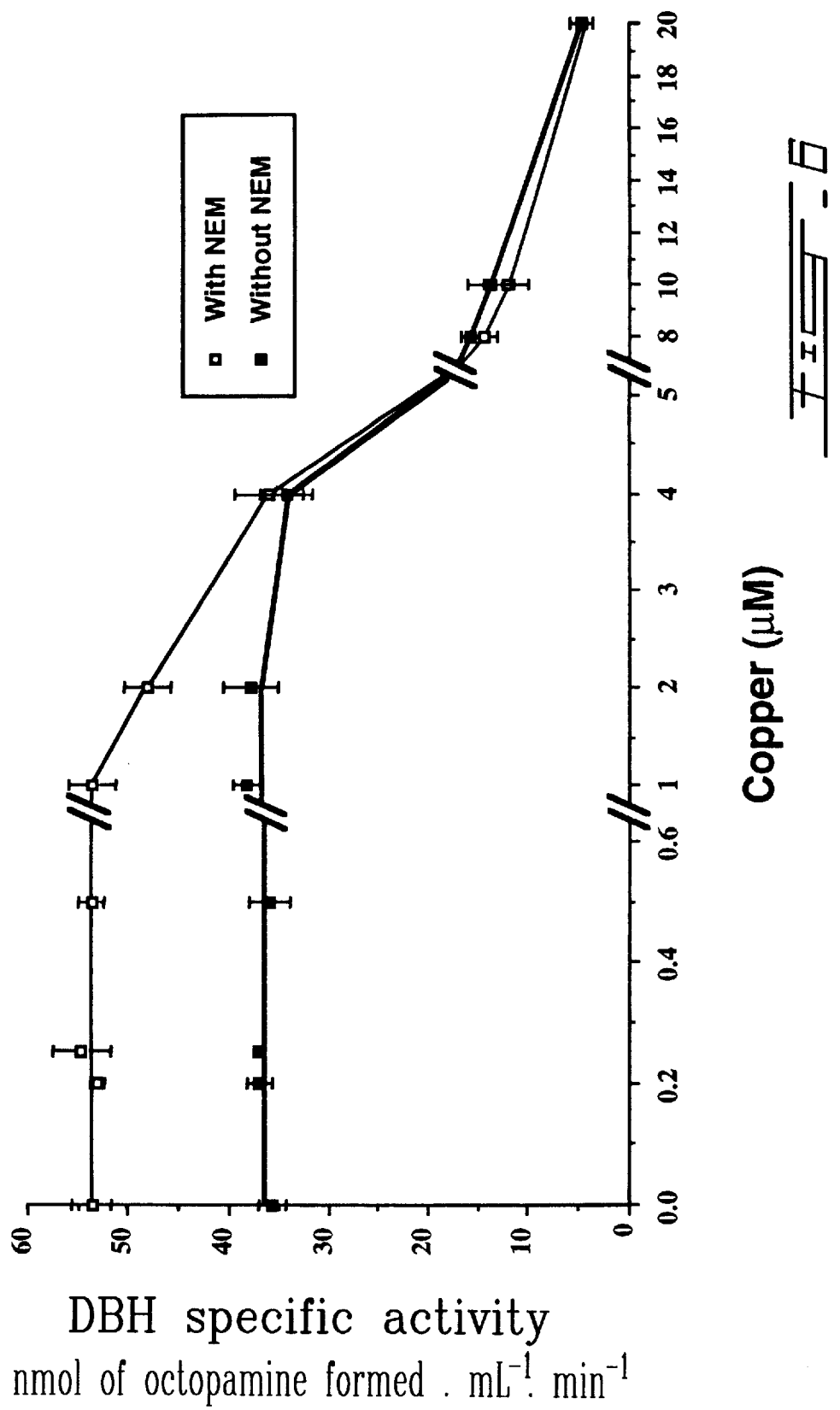

DIAGNOSTIC METHODS AND KITS FOR THE EVALUATION OF THE SYMPATHETIC NERVOUS SYSTEM FUNCTION

BACKGROUND OF THE INVENTION (a) Field of the Invention

The invention relates to diagnostic methods and kits for the evaluation of the sympathetic nervous system function based on the detection of dopamine-β-hydroxylase specific activity by photometrically determining the formation of octopamine from tyramine.

(b) Description of Prior Art

Dopamine-β-hydroxylase [DBH: 3,4-di-hydroxyphenylethylamine, ascorbate: oxygen oxydoreductase (β-hydroxylating) EC 1.14.17.1] as a mixed copper-dependent enzyme catalyses the hydroxylation of dopamine to norepinephrine (or noradrenaline) and its presence in the blood of humans and animals results from its localization within the catecholamines containing vesicules in the central and sympathetic nervous system and in the chromaffin granules of the adrenal medulla (Stewart LC et al., *Ann Rev Bioch*, 1988, 57:551–592).

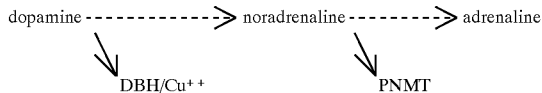

The properties and characterization of the serum purified enzyme have been well described in human and rate (Ikeno T et al., *Mol Cell Biochem*, 1977, 18(23):117–123). Serum DBH activity is biochemically and immunochemically similar to that present in other tissues whatever the species used and the existence of dissociated dimeric forms of DBH has been detailed in enzyme from purified human plasma or pheochromocytoma as glycoprotein and as copper-dependent enzymes. DBH is secreted with noradrenaline in the blood during a stimulation of the sympathetic nervous system. The secretion of DBH, noradrenaline and adrenaline is also repressed during an immunosuppressive situation. The dopamine-adrenaline pathway is affected in cases of neurodegenerative, neuroendocrine, psycho-affective and cardiovascular diseases, and in cases of burn-out, chronic fatigue as well as stressful situations such as panic syndrome.

The discovery of DBH in human blood led to the proposal that the serum activity may provide an index of sympathetic nervous system function in man (Geffen LB, *Life Sci*, 1974, 14(9):1593–1604). However, there exist no diagnostic assay for the direct determination of DBH to serve as a tool to evaluate the sympathetic nervous system function or the hypothalamic-pituitary-adrenal axis. The hypothalamic-pituitary-adrenal axis plays an important role in the body's ability to cope with stress such as infection, hypotension, immunodeficiency, surgery, psychoaffective disorders, neurodegenerative disorders. The hypothalamus pituitary couple is the "exit door" of the brain. The hypothalamus itself is subject to regulatory influences from other parts of the brain especially the mesolimbic system. The hypothalamic hormones corticotropin-releasing hormone and arginine vasopressin are important stimulants of corticotropin secretion by the anterior pituitary.

To date, clinical tests of the hypothalamic-pituitary-adreno-sympathetic (HPAS) axis and of hypothalamic-pituitary-adrenal (HPA) axis are based on the stimulation of pituitary adrenocorticotropin hormone (ACTH) release or adrenocorticol release of ACTH-dependent steroids to evaluate suspected adrenocortical insufficiency. Basically, none of the test available to date can evaluate the HPA axis. The most widely applied tests of the HPA axis are invasive and use short ACTH injection test (SAT), the insulin hypoglycemia test (IHT), the short metapyrone test (SMT) and the corticotropin-releasing hormone (CRH) test. Presently, the reliability of these tests in clinical settings is questioned under the aspect of dose-response relationship between plasma ACTH and cortisol in normal patient or subject excluding all relationship between cortisol and both noradrenaline and adrenaline involved in both HPA and HPAS axis themselves. The conventional clinical method of assessment of the HPA axis present the disadvantages, such as lack of sensitivity related to an indirect means of detection, costly and time consuming assay, circulating antibodies, not sensitive enough to allow for the detection of mild degrees of secondary adrenal insufficiency, and inappropriate for adrenal atrophy. There exist no clinically reliable test to measure an enzymatic activity involved in the dopamine-adrenaline pathway.

The reliability of these previous test in special clinical settings are questioned under several aspects such as dose-response relationships, specificity in respect to any form of adrenal insufficiency, for instance, sensitivity, complications, side-effects etc.. Until recently, clinical catecholamine neurochemistry has been used mainly to examine release of catechloamines as effector chemicals in order to indicate activities of peripheral neuronal system but a new approach based on understanding the clinical significance of catecholamine phenotypic changes such as serum DBH specific activity described in the present invention will be more and more in demand in order to provide potentially important clues to the diagnosis, treatment and pathophysiology of neurogenetic disorders. In this respect, it is necessary to develop clinical tool based on proteins participating in the synthesis, storage, release, metabolism and recycling of catecholamines and all related and in all related metabolic compounds involved in their homeostasis or biochemical balance.

It would be highly desirable to be provided with a clinical tool for the diagnostic of sympathetic nervous system function.

It would be highly desirable to be provided with a clinical tool for the diagnosis of neurodegenerative, neuroendocrine, psycho-affective and cardiovascular diseases, burn-out, chronic fatigue and panic syndrome.

SUMMARY OF THE INVENTION

One aim of the present invention is to provide a clinical tool for the diagnostic of sympathetic nervous system function and stress.

Another aim of the present invention is to provide a clinical tool for the diagnosis of neurodegenerative, neuroendocrine, psycho-affective and cardiovascular diseases, burn-out, chronic fatigue and panic syndrome.

In accordance with one embodiment of the present invention there is provided a diagnostic method for the evaluation of the sympathetic nervous system function based on the detection of dopamine-β-hydroxylase specific activity by spectrophotometrically determining the formation of octopamine from tyramine.

The "patient", in accordance with the present, includes without limitation, animals, such as domestic and herd animals, and human.

In accordance with one embodiment of the present invention there is provided an in vitro diagnostic method for the determination of specific dopamine-β-hydroxylase activity for the evaluation of the sympathetic nervous system function of a patient from a serum sample; which comprises the steps of:

a) filtering the serum sample to substantially remove drugs and endogenous inhibitors of dopamine-β-hydroxylase;

b) incubating the filtered sample of step a) with a substrate of dopamine-β-hydroxylase for conversion in a detectable compound;

c) determining the amount of detectable compound to evaluate dopamine-β-hydroxylase activity and comparing with a normal sample;

whereby an amount lower than a normal sample is indicative of a reduced sympathetic nervous system function and an amount higher than a normal sample is indicative of an increased sympathetic nervous system function.

In accordance with a further embodiment of the present invention there is provided an in vitro diagnostic method for the determination of specific dopamine-β-hydroxylase activity for the evaluation of the sympathetic nervous system function of a patient from a serum sample; which comprises the steps of:

a) filtering the serum sample to substantially remove drugs and endogenous inhibitors of dopamine-β-hydroxylase in a vial containing dry powder octopamine to obtain a sample solution;

b) incubating the sample solution with a substrate of dopamine-β-hydroxylase for conversion in a detectable compound;

c) determining the amount of detectable compound to evaluate dopamine-β-hydroxylase activity through a positively-charged resin and comparing with a normal sample;

whereby an amount lower than a normal sample is indicative of a reduce sympathetic nervous system function and an amount higher than a normal sample is indicative of an increased sympathetic nervous system function.

Preferably, the vial has an opening and comprises a removable filter tightly mounted at a distance from the octopamine in a dry powder. More preferably, the filter is mounted at the upper edge of the vial or at a distance between the upper edge and the octopamine solution. Also preferably, the filter has pores of about 100 μ.

In accordance with the methods of the present invention, the substrate is preferably tyramine and the detectable compound is preferably an octopamine derivative. More preferably, the substrate further includes a positively-charged resin for binding to the octopamine derivative thus avoiding manipulation and time-consuming.

The methods preferably further include a step between b) and c) wherein catalase is added for peroxide degradation, which could inhibit the enzyme activity or dopamine-β-hydroxylase activity.

Preferably, the octopamine derivative amount is determined by further adding $NaIO_4$ to the incubation medium and p-hydroxybenzaldehyde is spectrophotometrically measured.

In accordance with the methods of the present invention, a reduction in the sympathetic nervous system function is indicative of neurodegenerative, neuroendocrine, psychoaffective and cardiovascular diseases, burn-out, chronic fatigue and panic syndrome.

In accordance with the methods of the present invention, an increased in the sympathetic nervous system function is indicative of the effects of stress.

More precisely, the following pathologies are associated with a reduction in the sympathetic nervous system function:
schizophrenia;
psycho-affective disorders;
menstrual migraine;
hypotension;
heart failure; and
myocardial infarction.

More precisely, the following pathologies are associated with an increased in the sympathetic nervous system function:
acute cerebrovascular;
stress caused by starvation, food restriction, work load or cold stress;
hypertension; and
sympathetic hyperactivity.

In accordance with a further embodiment of the present invention there is provided a kit for the in vitro determination of dopamine-β-hydroxylase specific activity; which comprises the components of:

a) an octopamine solution-containing vial having a removable filter tightly mounted at a distance from the solution;

b) a substrate of dopamine-β-hydroxylase for conversion in a detectable compound; and c) a catalase solution.

Preferably, component a) further comprises a sodium acetate buffer and N-ethylmaleimide. Preferably, component b) comprises tyramine and ascorbate. More preferably, component b) further comprises disodium fumarate and pargyline.HCl.

BRIEF DESCRIPTION OF THE DRAWINGS

FIGS. 2–2A illustrates the effect of enzyme concentration on specific human DBH activity;

FIG. 3 illustrates the effect of tyramine concentrations on specific DBH activity in human serum;

FIG. 4 illustrates the effect of ascorbate concentrations on specific DBH activity in human serum;

FIG. 6 illustrates the effect of copper concentrations on specific DBH activity in human serum. Each square represents at least six determinations done on a pool of 25 subjects;

DETAILED DESCRIPTION OF THE INVENTION

Biochemical properties and kinetic parameters of dopamine-β-hydroxylase activity were measured in unpurified normal human serum. The enzyme activity was 1) ascorbate-dependent being saturated by exogenous 10 mM ascorbate: 2) independent to exogenous copper added leading to a significant decrease with concentrations higher than 4 µM; 3) saturated by 20 mM tyramine; 4) measured in as little as 1 to 20 µL of serum; 5) found to have a grater affinity for ascorbate than for tyramine; the Km value being 10 times lower than for tyramine; 6) significantly enhanced by 15 mM N-ethylmaleimide in the incubation medium; 7) similarly distributed in a group of male and female subjects aged between 15 to 85 years with no significant difference in respect to sex and age.

The diagnostic kit of the present invention is rapid, sensitive, simple and reproducible and the clinical values have a lower range of distribution than those reported n the literature, because the blood is filtered to avoid inhibitors and drugs interactions, thus suggesting this technique as a useful tool in clinical investigations. Moreover, the kit of the present invention allows quantitative determination of DBH specific activity in a small amount of blood sample without any interferences with usual related rugs taken by patients such as β-blockers, calcium blockers, etc.

Materials

Figure 9:
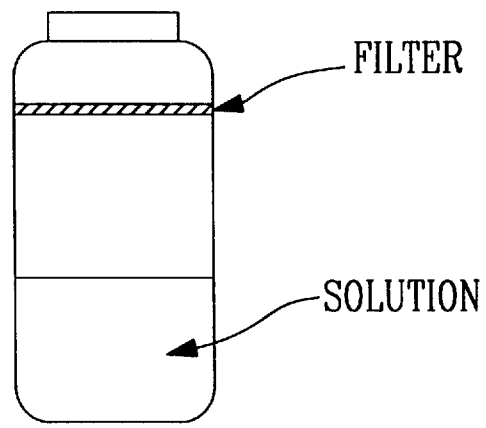
FIG. 9 illustrates a vial having a removable filter tightly mounted at a distance from the solution in accordance with one embodiment of the present invention.

Octopamine, L-tyramine, ascorbic acid, disodium fumarate, pargyline.HCl, sodium-m-periodate and N-ethylmaleimide (NEM) and bovine serum albumin were purchased from Sigma Co. (St-Louis, Mo. U.S.A.). Monobasic and dibasic sodium bisulfite were obtained from Fisher Scientific (Ste-Foy, Quëbec), beef liver catalase from DBH (Ville St-Laurent, Quëbec), DOWEX™ 50×4-400 from Aldrich Chemicals Co. (Milwaukee, Wis.) and the DIAFLO™ Ultrafilter membrane, type YM100, was purchased from Amicon Canada Ltd (Oakville, Ontario) which can be mounted on a vial as shown in FIG. 9.

Experimental procedures

Serum samples were withdrawn from 224 apparently healthy male (78) and female (146) subjects, without particular history of illness, alcoholism or drug abuse. Their serum samples were collected from 8:00 to 10:00 hours for usual clinical routine blood evaluation. All blood specimens were collected following venipuncture in the left arm, placed on ice and centrifuged at 10,000 g for 10 min at 4° C. The serum was removed and stored at −80° C. until dopamine-β-hydroxylase (DBH) activity was performed.

Enzyme Preparation

The kinetic parameters and biochemical properties were done on a pool of 25 subjects randomly distributed between males and females. An appropriate aliquot of serum was taken as enzyme source and diluted in ice-cold deionized water to a final volume of 400 µL, prior the preincubation period. For individual measurements of DBH enzyme activity, 20 µL of human serum was routinely used. For the ultrafiltration method, an aliquot of a pool of serum was passed through a DIAFLO™ Ultrafilter membrane, type YM100, and 40 µL of the ultrafiltrate was used to measure the enzyme activity (FIG. 9).

Enzyme Assays

The specific DBH activity was determined by the method described by Roberge and Charbonneau (Roberge AG et al., *Nutr Res*, 1985, 5:57–63). The preincubation mixture contained 0.2M sodium acetate buffer (pH 5), 15 mM N-ethylmaleimide (NEM) and the enzyme source (from the serum sample) and was carried out at 25° C. for 10 min in an atmosphere of air using a metabolic shaker (Dubnoff). To the preincubated enzymatic source were added to a final volume of 1 mL: 10 mM fumarate, 10M ascorbic acid, 2500 units catalase and 1 mM pargyline, as monoamide oxidasae inhibitor. Blanks and internal standards were set up in the same manner and contained 20 mM octopamine instead of the enzyme source. The incubation was started with 20 mM tyramine and conducted at 37° C. for 30 min in an atmosphere of air using a metabolic shaker (Dubnoff). The reaction was stopped on ice by adding 300 µL of 3M trichloroacetic acid to each tube and immediately centrifuged at 2500 g of at 4° C. for 10 min. The supernatant was decanted on a DOWEX™ 50×4-400 resin column and the acid eluted with 3M NH$_4$OH. The octopamine formed was derived to p-hydroxybenzaldehyde by periodate cleavage which was isolated by successive solvent extractions with ether and ammonia. The last aqueous phase was assayed by a dual-wavelenght spectrophotometer (333–360 nm). Specific activity was expressed n normal of octopamine formed per mL per min. Recovery of octopamine added to the blank incubation mixture was 90±2%. L-tyramine was used as substrate and an aliquot of unpurified serum was taken as the enzyme source, usually 20 µL.

Enzymatic kinetic

Apparent Michaelis constant (Km) and apparent maximum velocity (Vmax) were determined following the Woolf's graphical procedure and the usual method of Lineweaver and Burk. Statistical estimation related to enzyme kinetics was done according to Wilkinson.

Protein determination

Protein concentration was measured using bovine serum albumin as standard.

Statistical analysis

Means, standard deviation, standard error of the mean (SEM), Chi square test, paired-t-test and one-way ANOVA followed by a Duncan test were calculated. The difference between means were considered significant at P<0.05. The intra-essay coefficient of variation with this method is less than 1%. The replication of the data done on the same subjects through a period of 4 months was highly correlated (P<0.01).

RESULTS

The concentrations of protein were of 72±8 mg per mL of human serum obtained from 10 different pooled serum and of 16.5±2 mg of mL of ultrafiltrate. These values were retained for all estimations of the enzyme activity expressed in nmol of octopamine formed per mg of protein.

pH Dependence

Figure 1:
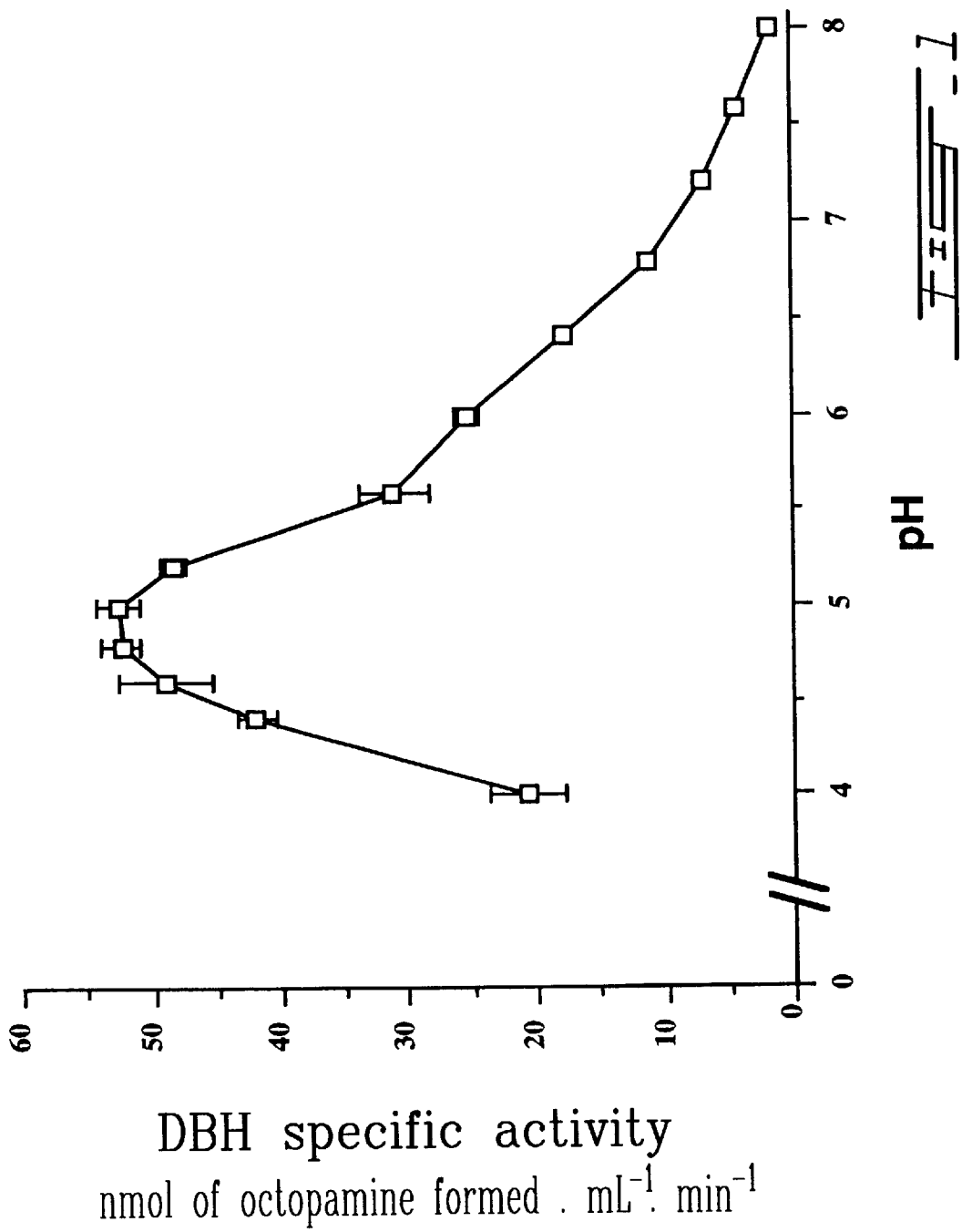
FIG. 1 illustrates the dependence upon pH of specific DBH activity in human serum.

In FIG. 1, the human serum specific DBH activity was determined using a range of pH from 4 to 8 with constant ascorbate (10 mM) and tyramine (20 mM) concentrations. Each square represents at least six determinations done on a pool of 25 subjects. The results are expressed in normal of octopamine formed per mL per min (mean±SEM). The enzyme activity reached maximum activity around pH 4.8 and 5.0 (<0.05) whereas a progressive and significant decrease was observed at pH over 5.2 (P<0.01; P<0.001). The specific enzyme activity (mean±SEM) was 55.5±5 nmol octopamine formed per mL per min at pH 5 an this pH was selected for all further experiments.

Incubation Time

The incubation time was tested for periods up to 60 min and the incubation was carried out at pH 5. The incubation mixture contained all components described in the previous section. The specific DBH activity was proportional to the incubation time during at least 60 min when results are expressed in nmol of octopamine formed per mL of serum. The incubation time chosen for all experiments was 30 min at 37° C.

The preincubation period was tested at 25° C. and 37° C., respectively. As no significant difference was observed n the measured enzyme activity, the temperature chosen for the preincubation period was 25° C.

Enzyme Concentration

Figure 2A:
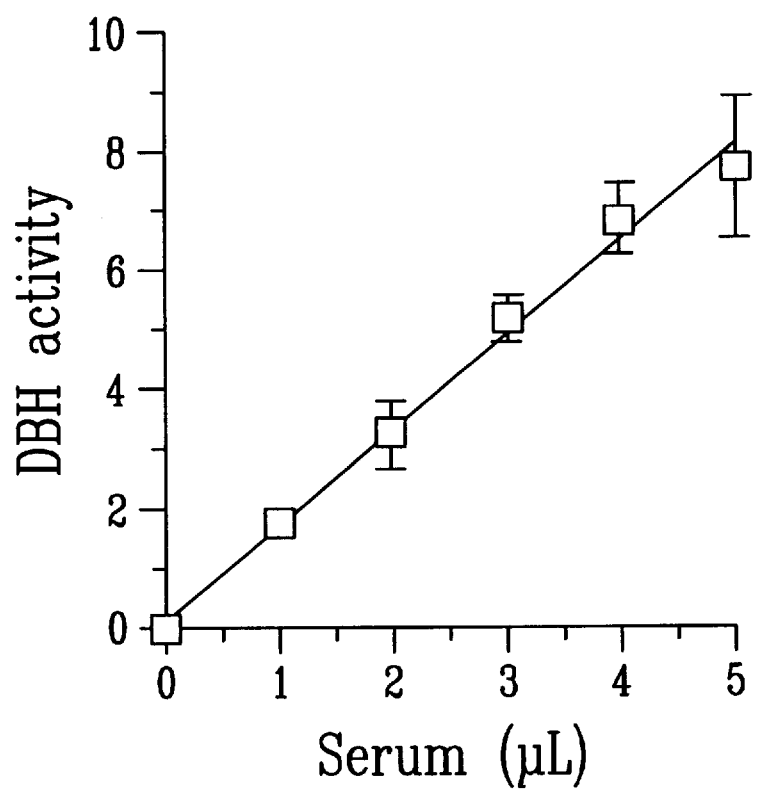

Different volumes of a pool of normal human serum, from 1–200 μL, were diluted in 400 μL of ice-cold water to measure the specific DBH enzyme activity. In FIG. 2, it is demonstrated that the enzyme activity is linear up to 50 μL of serum used and the window shows the enzyme activity measured in as little as 1–20 μL of serum (FIG. 2A). Each square represents at least six determinations done on a pool of 25 subjects. The results are expressed in normal of octopamine formed per 30 min (mean±SEM). For a linear reaction, the variation in the serum to ice-cold water dilution ratio was from 1:400 to 1:8. Each point on the graph represents at least six determinations done on a pool of normal serum. Results are expressed in nmol of octopamine formed per 30 min (mean±SEM).

Experiments done with large volumes of serum (from 50 to 100 μL) diluted in 400 μL of ice-cold water, have revealed that the linearity of the reaction was maintained by increasing from 15 to 30 mM the NEM content in the incubation medium. Between 100 to 200 μL of serum, the reaction was not linear whatever the NEM content in the medium. At anytime, the addition of copper in the medium contributes to restore the linearity of the reaction or to enhance the enzyme activity. All further experiments were carried out with 20 μL of serum diluted in 400 μL of ice-cooled water for a ratio of 1:20 in a 1 mL final volume of the incubation mixture as described above.

Tyramine Concentration

In FIG. 3, the effects of tyramine concentrations up to 30 mM on the specific DBH enzyme activity are shown with a constant 10 mM ascorbate content. Each square represents at least six determinations done on a pool of 25 subjects. The results are expressed in nmol of octopamine formed per mL per min (mean±SEM). Kinetic parameters of DBH in human serum for tyramine, as substrate. Km and Vmax values were calculated from plots of substrate concentration according to Woolf's graphical method.

A progressive increase related to the amounts of tyramine used (up to 15 mM) was demonstrated in the formation of octopamine followed by a plateau ($P<0.05$). Each point on the graph represents at least six determinations done on a pool of normal serum. Results are expressed in nmol of octopamine formed per mL per min (mean±SEM). The saturation point observed at 20 mM tyramine was retained for all further experiments using 20 μL of serum as enzyme source.

Ascorbate Dependence

In FIG. 4, the effects of ascorbate concentrations (0 to 30 mM) are demonstrated with a fixed 20 mM tyramine content in the incubation mixture. The enzyme activity was enhanced by ascorbate up to 10 mM ($P<0.01$), followed by a plateau ($P<0.05$; $P<0.01$). Each square represents at least six determinations done on a pool of 25 subjects. The results are expressed in nmol of octopamine formed per mL per min (mean±SEM). Kinetic parameters of DBH in human serum for ascorbate, as cofactor. Km and Vmax values were calculated from plots of ascorbate concentrations according to Woolf's graphic method. The saturation point obtained with 10 mM ascorbate was retained for all further experiments. In Table I, the enzyme activity measured without different components usually present in the incubation medium demonstrates that the omission of ascorbate in the medium led to a significant drop in the enzyme activity (96%; $P<0.001$).

TABLE I

SERUM DOPAMINE-B-HYDROXYLASE ACTIVITY:
EFFECTS OF COFACTORS

| Omissions ■ | Activity ++ | % Control |
|---|---|---|
| None (control) | 53.7 ± 0.18 | 100 |
| Ascorbate | 2.2 ± 0.19 | 4 |
| Catalase | 5.6 ± 0.45 | 10 |
| Fumarate | 47.5 ± 1.00 | 88 |
| N-ethylmaleimide (NEM) | 35.6 ± 0.39 | 66 |
| NEM and Fumarate | 36.2 ± 0.79 | 67 |

■ A pool of 25 normal human serum was used to measure DBH enzyme activity in the usual way (control) and in the absence of some ingredients of the reaction mixture described in Methods section.
++ Results are expressed as the mean of at least 10 determinations ± SEM in nmol of octopamine formed per mL per min at 37° C.

Catalase Concentration

Different concentrations of catalase were used to obtain the maximum enzyme activity. A progressive increase in the enzyme activity was observed with catalase up to 2000 units in the incubation medium ($P<0.01$) followed by a plateau till 4000 units. In Table I, the commission of catalase in the incubation medium has resumed the enzyme activity to 10% ($P<0.001$). For all further experiments, 2500 units of catalase were used.

Fumarate Concentration

Whatever the concentrations used, up to 40 mM, the addition of fumarate in the incubation medium led to a slight but significant increase in the enzyme activity (12%; $P<0.05$; Table I). The simultaneous omission of both fumarate and NEM in the incubation medium has significantly decreased the enzyme activity by 33% ($P<0.01$; Table I). For all further experiments, 10 mM fumarate was retained.

NEM Concentration

Figure 5:
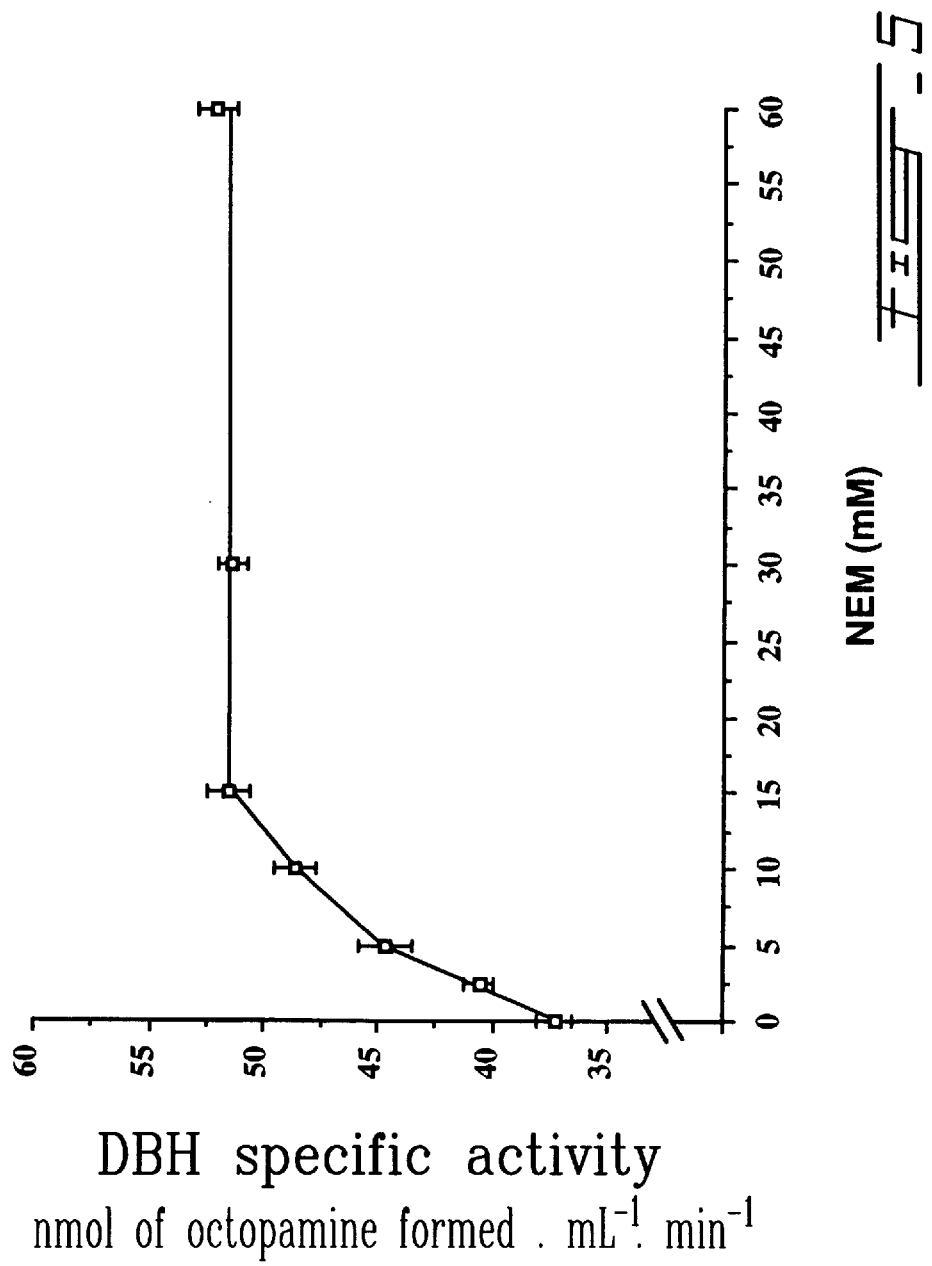
FIG. 5 illustrates the effect of N-ethylamelimide (NEM) concentrations on specific DBH activity in human serum.

In FIG. 5, the effects of different concentrations of NEM (Up to 60 mM) are described. Each square represents at least six determinations done on a pool of 25 subjects. The results are expressed in nmol of octopamine formed per mL per min (mean±SEM). The enzyme activity was significantly increased in the presence of NEM up to 1 5 mM ($P<0.01$) followed by a plateau till 60 mM. In Table I, it is demonstrated that the omission of NEM in the incubation medium has significantly decreased the enzyme activity by 36% ($P<0.01$). All further experiments were performed with 15 mM NEM in the incubation medium.

Exogenous Copper and NEM Interactions

The effects of different copper concentrations, ranging from 0 to 20 μL on specific DBH enzyme activity are described n the presence and absence of 15 mM NEM in the incubation medium, respectively (FIG. 6). The results are expressed in nmol of octopamine formed per mL per min (mean±SEM).

The results show that without NEM in the medium (FIG. 6, black squares), a significant drop in the enzyme activity was observed (66%; $P<0.01$) comparatively to the data obtained in the presence of NEM (FIG. 6, white squares). With NEM in the medium, the enzyme activity measured with exogenous copper concentrations up to 2 μM was not significantly different than the values obtained in its absence (FIG. 6, white squares). However, a progressive and significant decrease in the enzyme activity was observed with exogenous copper content higher than 2 μM ($P<0.05$) to a maximum decrease noted at 20 μM (90%; $P<0.001$).

Without PEM in the incubation medium, the addition of various copper concentrations up to 4 μM (FIG. 6, black squares) did not significantly change the enzyme activity comparatively to the data obtained without copper in the medium. However, with exogenous copper concentrations higher than 4 μM, a significant decreased enzyme activity was noted up to 20 μM (P<0.001). When the two curves are compared (FIG. 6, white and black squares), a significant difference in the enzyme activity is observed in the presence of exogenous copper concentrations up to 2 and 4 μM, respectively (P<0.001; P<0.05), but any significant difference was noted with higher copper concentrations. Each point on the graph represents at least six determinations done on a pool of normal serum. Results are expressed in nmol of octopamine formed per mL per min (mean±SEM). All further experiments were performed with 15 mM NEM but without copper in the incubation medium.

The relationship between copper and NEM in the medium was studied in an aliquot of serum passed through a DIAFLO™ Ultrafilter membrane, type YM100, and the enzyme activity was measured in the ultrafiltrate. The results show that the enzyme activity was not enhanced by the presence of 15 mM NEM in the medium, the activity being respectively of 52±0.7 and 50±0.6 nmol of octopamine formed per mg of protein per hour, with or without NEM. Moreover, the addition of copper in the medium up to 4 μM did not influence the enzyme activity leading to a decrease with higher concentrations, thus corroborating the results demonstrated in FIG. 6. The enzyme activity was of 51±0.56 nmol of octopamine formed per mg of protein per hour, with or without copper in the medium.

Kinetic Parameters

In FIGS. 3 and 4, the kinetic parameters were respectively calculated by the Woolf's graphical method in using different concentrations of tyramine (substrate) and ascorbate (cofactor) in the incubation medium. In human serum, at pH 5.0, the apparent Michaelis constant (Km) was of 8 mM for tyramine and the apparent Vmax value was of 72 nmol of octopamine formed per mL per min (FIG. 3) whereas the Km value calculated for ascorbate (FIG. 4) was of 0.77 mM, giving a maximum velocity of 56 nmol octopamine formed per mL per min.

Copper Chelation

Figure 7A:
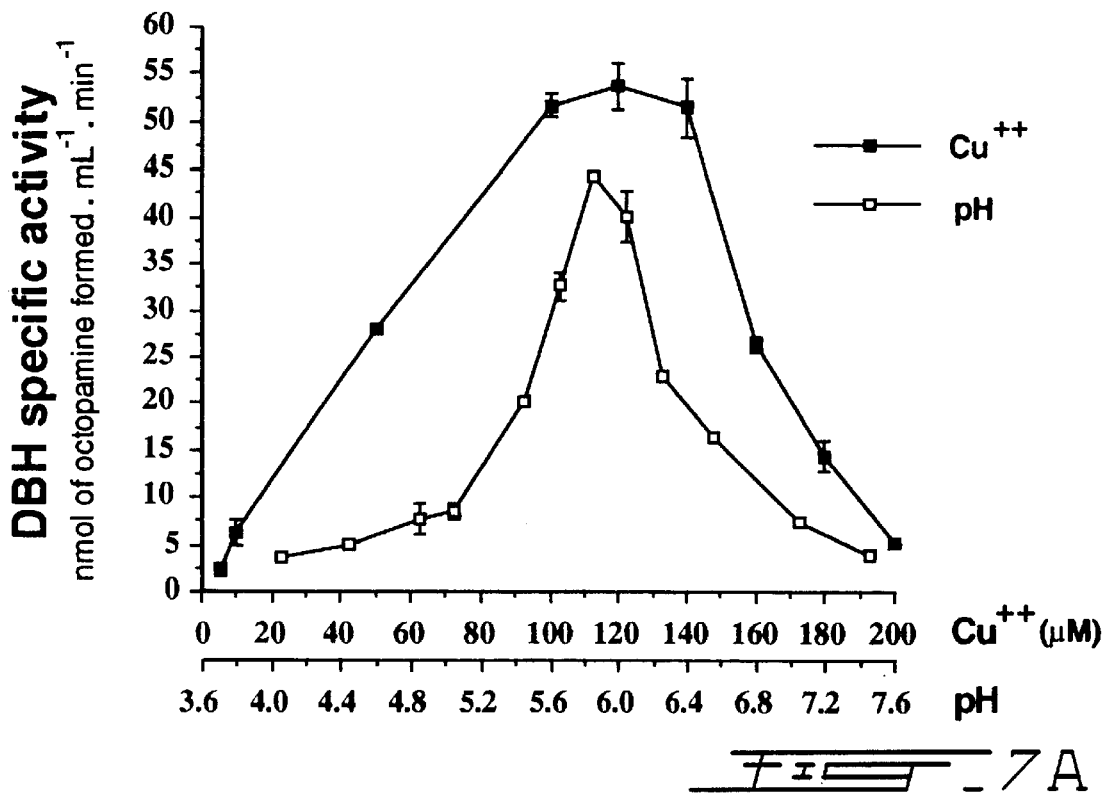
FIGS. 7–7A illustrates the biochemical properties and kinetic parameters of DBH activity measured in human EDTA-treated blood.
Figure 7B:
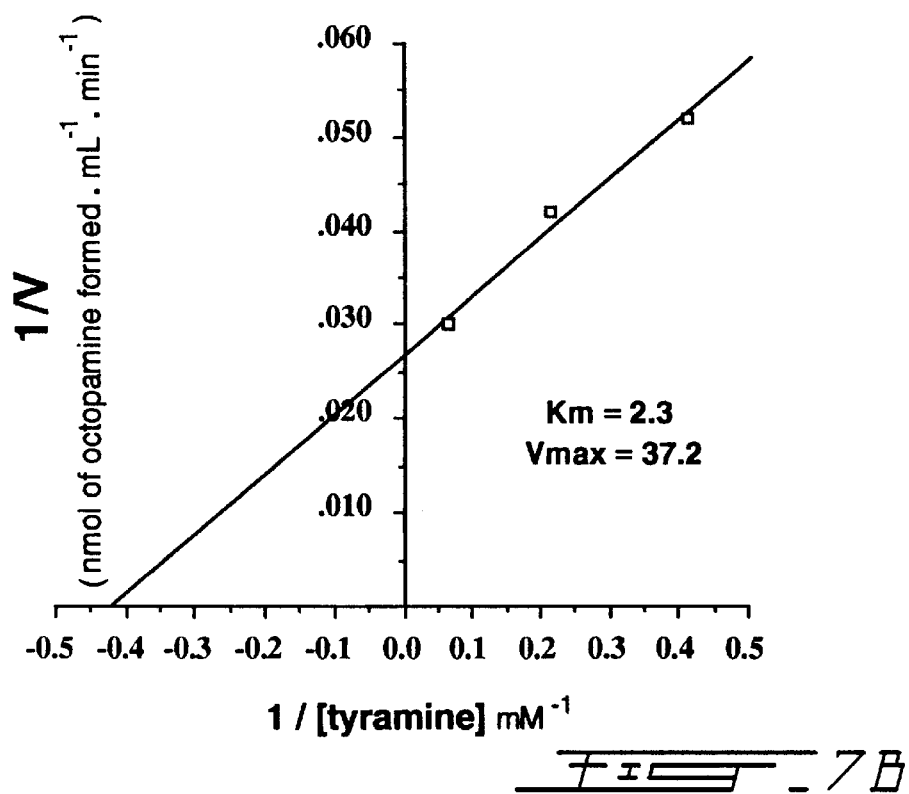

In FIG. 7A, the specific DBH enzyme activity was measured in human blood treated with EDTA, a copper chelator, in respect to pH dependence, to copper content added in the incubation medium and to kinetic parameters. Dependence upon pH, effect of copper concentration and, Km and Vmax values calculated according to Lineweaver and Burk are respectively demonstrated. The results are expressed in nmol of octopamine formed per mL per min (mean±SEM).

The EDTA inhibition was progressively reversed by the addition of exogenous copper in the medium from 0 to 100 μM followed by a decreased enzyme activity with copper concentrations higher than 140 μM (FIG. 7A, white squares). According to pH dependence, the optimal enzyme activity observed with EDTA-treated blood was at pH 5.8 instead of pH 5.0 (FIG. 7A, black squares). The Km and Vmax values measured at pH 5.8 in respect to tyramine, as substrate, were of 2.4 mM and 38.5 nmol of octopamine formed per mL per min, respectively (FIG. 7A), being significantly different (P<0.01) than the respective values observed with normal human serum (FIG. 3) for tyramine, as substrate.

Serum DBH in Healthy Male and Female Subjects

Figure 8:
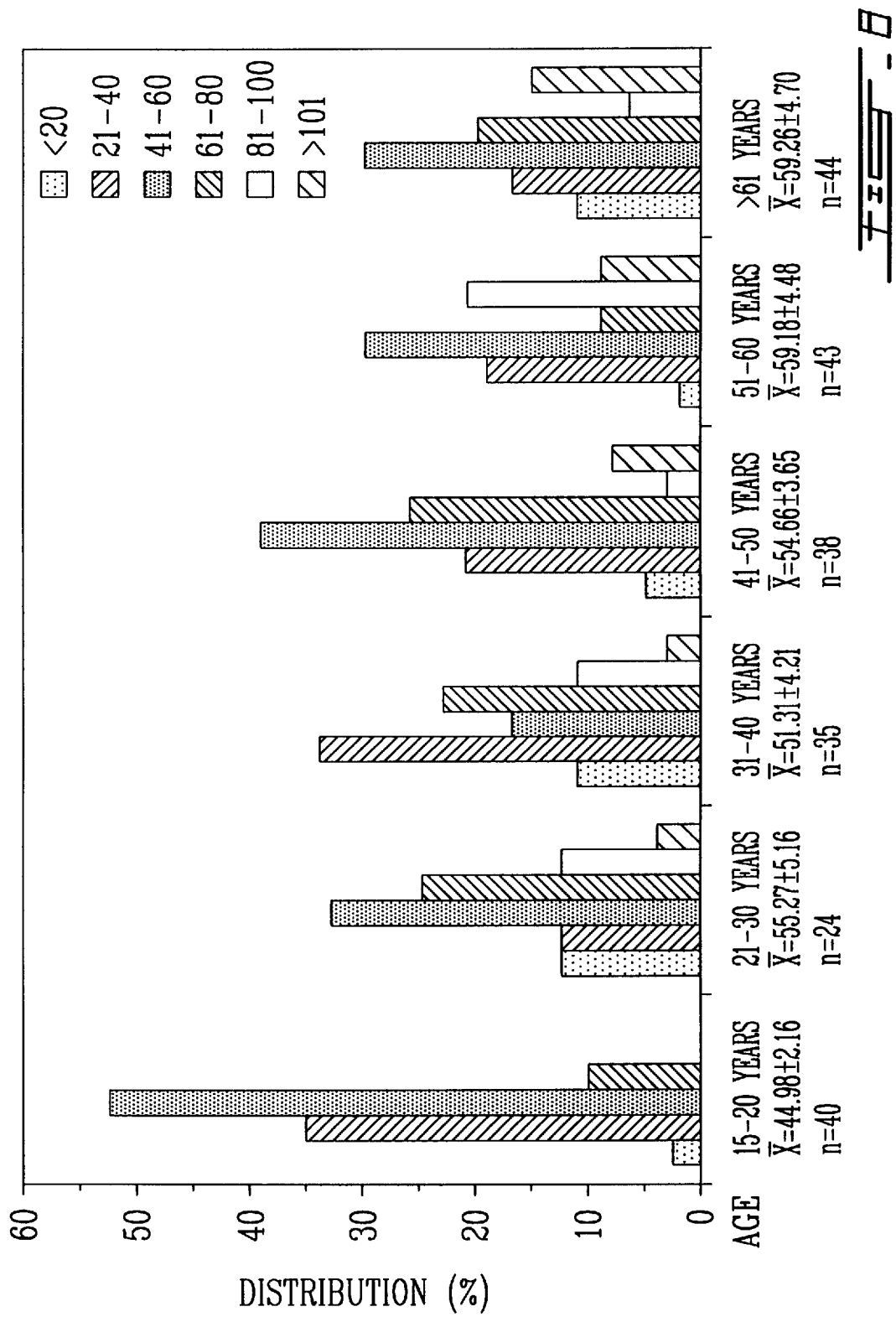
FIG. 8 illustrates the distribution (%) of serum DBH enzyme activity measured in normal healthy group of 224 subjects in respect to various age groups.

In FIG. 8, the human serum DBH enzyme activity, measured in 224 apparently healthy male and female subjects, is described according to different age groups (aged between 15 and 85 years). Results are expressed in nmol of octopamine formed per mL per min (mean±SEM). For each age groups, the number of subjects is in parenthesis. Subjects were grouped according to enzyme activity (<20: 21–40; 40–60; 61"80; 81–100; <100) expressed in nmol of octopamine formed per mL per min (mean±SEM).

The enzyme activity was routinely measured in 20 μL of serum as described in the Methods section. Triplicates were done on each sample and the intra-assay coefficient of variation was less than 1%. the enzyme activity measured on the same subjects through a period of 4 months was highly correlated (P<0.01). The results show a similar distribution in respect to age groups without any significant difference within the groups.

In Table II, the clinical values (mean±SEM; range of distribution) of serum DBH enzyme activity are described in respect to age groups, in female (146) and male (78) subjects, respectively. For the whole group, any significant difference in the enzyme activity was observed in respect to sex and age and the data show a range of distribution varying from 2 to 138 nmol of octopamine formed per mL per min. Within the female and male groups, any significance difference was observed in respect to the range of distribution. All statistical analysis done to compare male and female subjects in respect to their corresponding age groups were not significant at P<0.05.

TABLE II

CLINICAL VALUES OF SERUM DBH ACTIVITY IN FEMALE AND MALE SUBJECTS IN RESPECT TO AGE AND SEX*

| Age Groups | | Females | | Males |
|---|---|---|---|---|
| 15–20 years | (35) | 44.6 ± 2.0 | (5) | 47.4 ± 10.9 |
| range | | 27–76 | | 11–79 |
| 21–30 years | (20) | 53.4 ± 6.0 | (4) | 64.6 ± 6.1 |
| range | | 13–108 | | 52–81 |
| 31–40 years | (23) | 51.0 ± 5.6 | (12) | 51.8 ± 6.4 |
| range | | 12–111 | | 21–87 |
| 41–50 years | (22) | 60.7 ± 5.1 | (16) | 46.3 ± 4.4 |
| range | | 24–113 | | 16–77 |
| 51–60 years | (21) | 61.9 ± 7.1 | (22) | 56.6 ± 5.7 |
| range | | 17–122 | | 15–114 |
| 60–80 years | (26) | 65.9 ± 8.6 | (19) | 55.4 ± 6.2 |
| range | | 3–138 | | 19–133 |

*Results are expressed in nmol of octopamine formed per mL of serum per min (mean ± SEM) and the range of distribution is shown below the mean. Parenthesis represents the number of subjects used.

DISCUSSION

In accordance with the present invention, the biochemical parameters and kinetic properties of DBH enzyme activity are measured in unpurified normal human serum and the clinical values of serum DBH enzyme activity obtained from a group of apparently healthy male and female subjects and measured in respect to age and sex, thus contributing to define a sensitive and reproducible method to be used in clinical investigations.

Biochemical Studies

The biochemical properties and the kinetic parameters of DBH enzyme activity measured from a pool of human serum allows us to demonstrate that 1) the optimum pH dependence upon DBH activity was fixed at 5.0; 2) the saturating point for tyramine was 20 mM; 3) with or without NEM in the medium, the enzyme was independent upon the exogenous copper; 4) the presence of NEM in the medium has enhanced the enzyme activity and stabilized the reaction; 5) the enzyme was ascorbate dependent; 6) the enzyme activity was measured in as little as 1–20 μL of serum, the linearity of the reaction being observed with up to 50 μL of serum; 7) the kinetic parameters for tyramine and ascorbate was different demonstrating a greater affinity for ascorbate than for tyramine. The present results provide good evidence that, with unpurified human serum as enzyme source, the relationship between ascorbate and copper as exogenous cofactors of the enzymatic reaction was different, the enzyme being ascorbate-dependent. Moreover, the presence of NEM in the incubation medium is suffisant to take in charge all soluble endogenous sulfhydryl inhibitors thus resuming the role of copper in human serum as an endogenous cofactor bound to the active site of the enzyme, as demonstrated by EDTA chelation.

Kinetic studies

Structure and function of dopamine-β-hydroxylase (DBH) of human serum have been extensively studied by Frigon and Stone (Frigon RP et al., *J Biol Chem*, 1978, 253(19):6780–6786) as well as the kinetic parameters and the biochemical properties of the pure enzyme (Keno T et al., *Mol Cell Biochem*, 1977, 18(23):117–123). In respect to pH dependence and to tyramine saturation point, the present results are in good agreement with the previous data observed in human serum as well as in rate serum, in cat and rat adrenals (Fortin D et al., *Comp Biochem Physiol*, 1993, 104B(3):567–575) and in bovine chromaffin granules (Stewart LC et al., *Ann Rev Bioch*, 1988, 57:551–592). According to ascorbate concentrations, the Km value was ten-fold lower than for tyramine concentrations thus suggesting that the enzyme has a greater affinity to ascorbate, as cofactor, in human serum (Keno T et al., *Mol Cell Biochem*, 1977, 18(23):117–123; Frigon RP et al., *J Biol Chem*, 1978, 253(19): 6780–6786), as also observed in cat and rat adrenals (Fortin D et al., *Comp Biochem Physiol.* 1993, 104B(3):567–575) and in bovine adrenal medulla (Stewart LC et al., *Ann Rev Bioch*, 1988, 57:551–592). Moreover, the Vmax values for tyramine and ascorbate were in the same order of magnitude being similar to the activities reported for human serum but significantly higher than the values reported in the serum of other species (Geffen LB, *Life Sci*, 1974, 14(9):1593–1604). According to the present results, it is obvious to pinpoint that the kinetic parameters of DBH enzyme observed for ascorbate cannot be ascribed to insuffisant cooper since the exogenous copper content did not stimulate the enzyme activity, whatever the concentrations used and with or without NEM in the medium.

Dependence upon exogenous ascorbate

In human serum, the present study demonstrates that the omission of ascorbate in the incubation medium resumed the enzyme activity at 4% as reported in the literature and also observed with various tissues (Fortin D et al., *Comp Biochem Physiol*, 1993, 00(0):305–491). Moreover, the enzyme-ascorbate complex has to be in the presence of catalase to prevent peroxide formation in the medium (Frigon RP et al., *J. Biol Chem*, 1978, 253(19):6780–6786) and to maintain the optimal enzyme activity. In bovine adrenals, it has been reported that external ascorbate prevents the depletion of the internal reduced ascorbate pool under hydroxylating conditions, thus suggesting a regulatory role for ascorbate in the level of DBH activity (Menniti F et al., *J Biol Chem.*, 1986, 261(36):16901–16908). Previous findings have also demonstrated that fumarate acts as a modulator and that anions structurally unrelated to fumarate such acetate and chloride exert a physiologically important role on DBH enzyme activity. In this respect, the present work shows that fumarate has slightly but significantly enhanced the enzyme activity, thus corroborating the literature towards the physiological role of anions in the reaction and emphasizing the role of anions such as chloride already present in all medium incubations to potentiate the enzyme activity together with fumarate.

Relationship between NEM and copper

In human serum, the presence of naturally occurring inhibitors of DBH enzyme led to the systematically addition of NEM, a sulfhydryl reactive agent, in the incubation medium (Geffen LB, *Life Sci*, 1974, 14(9):1593–1604) as well as in several other tissues. According to the present data, the sulfhydryl compounds did not compete with the substrate, tyramine, or the cofactor, ascorbic acid, but inhibit the enzyme activity by competing with the cysteine groups which maybe ligands of the protein-bound copper in regulating the enzyme activity. In this respect, the concentrations of NEM used to be effective in the incubation medium are relatively high (15 mM) thus demonstrating that ligands did not undergo to chemical modifications. Moreover, the present data observed in human serum are in good agreement with the general statement saying that the endogenous copper is weakly bound to the active site of enzyme, undergoing exchange and loss in the course of purification and being removed with chelators in which cases the addition of exogenous copper was necessary. In this respect, the experiments performed with EDTA-treated blood, as enzyme source, have clearly demonstrated the active role of copper on the site of the enzyme since a reversed inhibition was only observed with excess copper in the medium (100 μM), thus suggesting that EDTA in chelating the endogenous copper bound to the enzyme site has induced a reversible mechanism that only exogenous copper could counteract. These results arouse interest since, with purified and semi-purified enzyme sources, the addition of exogenous copper n the medium was necessary to replenish the loss due to the purification steps (Ikeno T et al., *Mol Cell Biochem.* 1977, 18(23): 117–123; Frigon RP et al,. *J Biol Chem.* 1978, 253(19):6780–6786) and thus was routinely done. Moreover, to study the interaction between exogenous copper and NEM in the medium as well as drugs interaction, an ultrafiltration method used to eliminate soluble molecules present in the enzyme source, with a molecular weight below 100,000, revealed that exogenous copper did not stimulate the enzyme activity deprived of its soluble inhibitors as observed with normal human serum thus emphasizing its action through the active site of the enzyme and eliminating the need of an exogenous addition in physiological conditions.

NEM a stabilizating agent

The relationship between NEW and copper in the enzymatic reaction with unpurified human serum, as enzyme source, was sparingly studied. On a clinical point of view, the present work corroborates the previous data done in human blood demonstrating that the real maximum velocity of the reaction was noted in the absence of copper in the medium in human serum but such observation could not be applied to rat and guinea pigs serum, respectively, the dissociating the enzyme activity in respect to species. The discrepancies in the literature towards clinical values of DBH enzyme activity were related to various factors such as the volumes of serum used, the concentrations of NEM in the medium and the presence or absence of exogenous copper in the medium, such factors have contributed to the disparity of the clinical data and to their repetitivity. In this respect, the ultrafiltration method used to measure the enzyme activity in the absence of soluble endogenous inhibitors of the enzyme has nullified the activatory action of NEM on the enzyme activity thus emphasizing its role towards the soluble sulfhydryl compounds present in the normal human serum. The relationship between the NEM content and the volume of human serum used before the icecold water dilution step was found crucial for the repetitivity of the data and the reproducibility of the method. Moreover, if more than 50 μL of serum were used to measured DBH enzyme activity, the linearity of the reaction has to be redefined in respect to the amount of NEM in the medium or to new optimal kinetic conditions. It is obvious to pinpoint that the ratio of the ice-cold water dilution step of serum has to be at least of 1:8 to respect the linearity of the reaction as well as the kinetic parameters and the biochemical properties already described. In these optimal conditions, the present method in using as little as 1–20 μL of human serum has cleary demonstrated that the Vmax values were at least 20% higher than the values reported in the literature, for human serum.

Clinical Studies

The present work demonstrates that the serum DBH enzyme activity measured in 224 apparently healthy male and female subjects was 1) similarly spread in male and female groups with a narrow range of distribution; 2) not significantly different in respect to age and sex; 3) not significantly different between males and females in any age group and, 4) highly correlated in respect to the replication of the data for individual subjects.

Healthy male and female subjects

The present clinical work was conduced in order to define the human serum DBH enzyme activity as a clinical tool in diagnosis investigations as suggested in the literature (Geffen LB, *Life Sci,* 1974, 14(9):1593–1604; Ogihara T et al., *J Lab Clin Med,* 1975, 85(4): 566–575) on the basis of a specific and valuable biochemical study and of statistically reproducible clinical data. Several clinical experiments were done to elucidate the mechanisms of the enzyme in different physiological states and to investigate its activity in various pathological states. Nevertheless, most of these clinical investigations would have to be conducted to a larger extent to be conclusive and to avoid the disparities of the clinical values related to various assay methods (Laduron P, *Biochem Pharmacol,* 1975, 24(5):557–562), duration, sampling procedures, selection of subjects and to variations in DBH activity within as well as between individuals due to the absence of valuable kinetic studies leading to a large interpretation of the data (Geffen LB, *Life Sci,* 1975, 14(9):1593–604; Ogihara T et al., *J Lab Clin Med,* 1975, 85(4):566–575).

The present measurements of human serum DBH enzyme activity in apparently healthy subjects are similar to those observed in published investigations using unpurified serum as enzyme source, omitting exogenous copper in the medium, adding NEM as well as tyramine at saturation point. The preincubation step has allowed to enhance the specific enzyme activity by 20% comparatively to those reported in the literature. Consequently, the present clinical values are significant higher than those published with excess copper in the medium and with treated plasma or large volumes of serum (100 μL and more). In this respect, it is noteworthy to mention that the human DBH enzyme activity measured in using a coupled-enzyme phenyl-N-methyl-transferase (PNMT) method to evaluate the adrenaline formed have given different results. In fact, this method involves two different kinetic measurements that are not necessarily optimal in the same conditions and for these reasons, the coupled enzymatic method as seriously questioned.

The present clinical values have demonstrated that the DBH enzyme activity was similar in male and female subjects and was not significantly different in regards to various age groups, as also reported in the literature. In fact, in the largest studies made of a normal population (Ogihara T et al., *J Lab Clin Med,* 1975, 85(4):566–575; Weinshilboum RM et al., *Science,* 1973, 181(4103):943–945; Sapru MK et al., *Acta Psychiatr Scand,* 1989, 80:474–478; Fujita F et al., *J Neurochem,* 1978, 30:1569–1572) of various age groups, it was demonstrated that the DBH enzyme activity was not significantly different through the adulthood but a continuing rise with age was correlated to the development of erect posture (Fujita F et al., *J Neurochem,* 1978, 30:1569–1572), during the first years of life. There were no significant differences between males and females in any age groups (Ogihara T et al., *J Lab Clin Med,* 1975, 85(4):566–575). However, the range of distribution of the present samples was not as broad as the one reported in the literature (from 13 to 1043 U/mL): being from 11 to 130 with the 78 males subjects and from 2 to 138 within the 146 female subjects. In the literature, the wide difference among subjects in DBH enzyme activity was argued to be genetically controlled (Geffen LB, *Life Sci,* 1974, 14(9):1593–1604; Weinshilboum RM et al., *Science,* 1973, 181(4103):943–945; Galvin M et al., *Psychiatry Res,* 1991, 39:1–11), knowing that any within-subject changes were observed as also noted in the present study. It is obvious to pinpoint that the specific serum DBH enzyme activity measured in mice, rats, guinea pigs, cats, bovine and in various primates was in the range of pmol per mL per min, being significantly lower than the values observed in human serum. Moreover, the enzyme activity measured in respect to age has showed a progressive increase in primates, from birth through the life-span, whereas in rats, the enzyme activity was significantly higher in females than in males demonstrating a minimum activity during the first days of postnatal life followed by a progressive increase reached at the age of 40 days maintained throughout the whole life-span.

In the present work, the samples collection was technically controlled and the manutention well respected in regards to routine clinical procedures thus contributing to the replication of the data according to time and avoiding intratechnical variations. The present improved method is simple, rapid, specific, reproducible and more sensitive than the previous ones and could be routinely introduced in a workshop station table currently used in clinical investigations. In this respect, the present technique might be considered as a clinical tool to be used in various diagnosis and as an index of the sympathetic nervous system activity.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An in vitro diagnostic method for the determination of specific dopamine-β-hydroxylase activity for the evaluation of the sympathetic nervous system function of a patient from a serum sample; which comprises the steps of:

a) filtering the serum sample to substantially remove drugs and endogenous inhibitors of dopamine-β-hydroxylase;

b) incubating the filtered sample of step a) with a substrate of dopamine-β-hydroxylase for conversion in a detectable compound;

c) determining the amount of detectable compound to evaluate dopamine-β-hydroxylase activity and comparing with a normal sample;

whereby an amount lower than a normal sample is indicative of a reduced sympathetic nervous system function and an amount higher than a normal sample is indicative of an increased sympathetic nervous system function.

2. The method of claim 1, wherein said substrate is tyramine and said detectable compound is an octopamine derivative.

3. The method of claim 2, wherein said substrate further include a positively-charged resin for binding to the octopamine derivative.

4. The method of claim 3, which further comprises a step between b) and c) wherein catalase is added for peroxide degradation.

5. The method of claim 4, wherein said octopamine derivative amount is determined by further incubating with $NaIO_4$ and p-hydroxybenzaldehyde is spectrophotometrically measured.

6. A method of claim 4, wherein when the sympathetic nervous system function is reduced indicates neurodegenerative, neuroendocrine, psycho-affective and cardiovascular diseases, burn-out, chronic fatigue, stress and panic syndrome.

7. A method of claim 4, wherein when the sympathetic nervous system function is increased indicates the effects of stress.

8. An in vitro diagnostic method for the determination of specific dopamine-β-hydroxylase activity for the evaluation of the sympathetic nervous system function of a patient from a serum sample; which comprises the steps of:

a) filtering the serum sample to substantially remove drugs and endogenous inhibitors of dopamine-β-hydroxylase in a vial containing dry powder octopamine to obtain a sample solution;

b) incubating the sample solution with a substrate of dopamine-β-hydroxylase for conversion in a detectable compound;

c) determining the amount of detectable compound to evaluate dopamine-β-hydroxylase activity through a positively-charged resin and comparing with a normal sample;

whereby an amount lower than a normal sample is indicative of a reduced sympathetic nervous system function and an amount higher than a normal sample is indicative of an increased sympathetic nervous system function.

9. The method of claim 8, wherein said vial has an opening and comprises a removable filter tightly mounted at a distance from said octopamine solution.

10. The method of claim 9, wherein said filler is mounted at the upper edge of said vial or at a distance between the upper edge and the octopamine dry powder.

11. The method of claim 10, wherein the filter is a membrane YM100™ or has pores to allow molecules of molecular weight below 100 000.

12. The method of claim 11, wherein said substrate is tyramine and said detectable compound is an octopamine derivative.

13. The method of claim 12, wherein said substrate further include a positively-charged resin for binding to the octopamine derivative.

14. The method of claim 13, which further comprises a step between b) and c) wherein catalase is added for peroxide degradation.

15. The method of claim 14, wherein said octopamine derivative amount is determined by further adding $NaIO_4$ and p-hydroxybenzaldehyde is spectrophotometrically measured.

16. A method of claim 15, wherein when the sympathetic nervous system function is reduced indicates neurodegenerative, neuroendocrine, psycho-affective and cardiovascular diseases, burn-out, chronic fatigue and panic syndrome.

17. A method of claim 15, wherein when the sympathetic nervous system function is increased indicates the effects of stress.

18. A kit for the in vitro determination of dopamine-β-hydroxylase specific activity according to claim 8; which comprises the components of:

a) an otopamine solution-containing vial having a removable filter tightly mounted at a distance from said solution;

b) a substrate of dopamine-β-hydroxylase for conversion in a detectable compound; and c) a catalase solution.

19. The kit of claim 18, wherein component a) further comprises a sodium acetate buffer.

20. The kit of claim 18, wherein component b) comprises tyramine and ascorbate.

21. The kit of claim 19, wherein component b) further comprises disodium fumarate and pargyline.HCl.

* * * * *